(12) United States Patent
Dawkins et al.

(10) Patent No.: US 10,697,015 B2
(45) Date of Patent: *Jun. 30, 2020

(54) METHODS OF GENOTYPING LIVESTOCK

(71) Applicant: CY O'Connor ERADE Village Foundation, Canning Vale South (AU)

(72) Inventors: Roger Letts Dawkins, Forrestdale (AU); John Anthony Millman, Shoalwater Bay (AU); Joseph Frederick Williamson, Victoria Park (AU); Patrick Robert Carnegie, Salter Point (AU)

(73) Assignee: CY O'CONNOR ERADE VILLAGE FOUNDATION (AU)

( * ) Notice: Subject to any disclaimer, the term of this patent is extended or adjusted under 35 U.S.C. 154(b) by 127 days.

This patent is subject to a terminal disclaimer.

(21) Appl. No.: 16/110,989

(22) Filed: Aug. 23, 2018

(65) Prior Publication Data
US 2019/0055601 A1 Feb. 21, 2019

Related U.S. Application Data

(60) Continuation of application No. 14/935,546, filed on Nov. 9, 2015, now abandoned, which is a division of
(Continued)

(30) Foreign Application Priority Data

Sep. 17, 2009 (AU) ................. 2009904511

(51) Int. Cl.
C12Q 1/68 (2018.01)
C12Q 1/6876 (2018.01)
C12Q 1/6883 (2018.01)

(52) U.S. Cl.
CPC ......... *C12Q 1/6876* (2013.01); *C12Q 1/6883* (2013.01); *C12Q 2600/124* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS 7,157,231 B2   1/2007   Mitsuhashi et al.
7,238,479 B2   7/2007   Smith et al.
(Continued)

FOREIGN PATENT DOCUMENTS

CA   2441938   10/2002
EP   1845159   10/2007
(Continued)

OTHER PUBLICATIONS

Surks et al., Myosin phosphatase-Rho interacting protein. A new member of the myosin phosphatase complex that directly binds RhoA, J Biol Chem. Dec. 19, 2003;278(51):51484-93. Epub Sep. 23, 2003.*

(Continued)

*Primary Examiner* — Aaron A Priest
(74) *Attorney, Agent, or Firm* — Sheridan Ross P.C.

(57) ABSTRACT

The present invention relates to methods of genotyping for selecting an animal with a desired trait such as the level monounsaturated fats in muscle tissue, the types and/or ratio of different monounsaturated fats in muscle tissue, marbling, carcass weight, meat quality, speed of finishing, feedlot efficiency and/or consumer preference. In particular the invention relates to methods of selecting an animal with a
(Continued)

desired trait by analysing the M-RIP, NT5M and/or TCAP genes for one or more polymorphisms.

21 Claims, 11 Drawing Sheets

Specification includes a Sequence Listing.

Related U.S. Application Data application No. 13/496,607, filed as application No. PCT/AU2010/001214 on Sep. 17, 2010, now Pat. No. 9,181,585.

(56) References Cited

U.S. PATENT DOCUMENTS

| | | | |
|---|---|---|---|
| 9,181,585 | B2 | 11/2015 | Dawkins et al. |
| 2002/0137139 | A1 | 9/2002 | Byatt et al. |
| 2004/0180811 | A1* | 9/2004 | Mendelsohn .......... C07H 21/04 |
| | | | 435/196 |
| 2004/0261138 | A1 | 12/2004 | Rothschild et al. |
| 2005/0137805 | A1* | 6/2005 | Lewin .................. C12Q 1/6809 |
| | | | 702/19 |
| 2005/0138679 | A1 | 6/2005 | Mitsuhashi et al. |
| 2007/0031845 | A1 | 2/2007 | DeNise et al. |
| 2007/0099209 | A1 | 5/2007 | Clarke et al. |
| 2008/0010696 | A1* | 1/2008 | Tsuji .................. C07K 14/4702 |
| | | | 800/15 |
| 2009/0010908 | A1 | 1/2009 | Gow et al. |
| 2015/0089691 | A1 | 3/2015 | Guo et al. |
| 2016/0281162 | A1 | 9/2016 | Dawkins et al. |

FOREIGN PATENT DOCUMENTS

| | | |
|---|---|---|
| JP | 2008125421 | 6/2008 |
| KR | 1020080090621 | 10/2008 |
| WO | WO 91/05853 | 5/1991 |
| WO | WO 2004/061125 | 7/2004 |
| WO | WO 2009/009439 | 1/2009 |
| WO | WO 2009/055805 | 4/2009 |

OTHER PUBLICATIONS

"Entrez SNP database: rs110111322", ARS-BGGL-NGS-64924, 2008, 1 page.
"Entrez SNP database: rs110930738", BTR-chr19_36053843, 2009, 2 pages.
"Entrez SNP database: rs111016377", BTR-chr19_36025334, 2009, 2 pages.
"1988 Catalog: Gene Characterization Kits," Stratagene, 1988, 2 pages.
Bhuiyan et al., "DNA Polymorphisms in SREBF1 and FASN Genes Affect Fatty Acid Composition in Korean Cattle (Hanwoo)," J. Anim, Sci., 2009, vol. 22(6), pp. 765-773.
Buck et al., "Design Strategies and Performance of Custom DNA Sequencing Primers," BioTechniques, 1999, vol. 27(3), pp. 528-536.
Carraro et al., "Expression profiling of skeletal muscle in young bulls treated with steroidal growth promoters," Physiol Genomics, vol. 38, 2009, pp. 138-148.
Cheong et al., "Titin-cap (TCAP) polymorphisms associated with marbling score of beef", Meat Science, 2007, vol. 77, pp. 257-263.
Hayashi et al., "Tcap Gene Mutations in Hypertrophic Cardiomyopathy and Dilated Cardiomyopathy," Journal of the American College of Cardiology, vol. 44, No. 11, 2004, pp. 2192-2201.
Hoashi et al., "Genotype of bovine sterol regulatory element binding protein-1 (SREBP-1) is associated with fatty acid composition in Japanese Black cattle," Mammalian Genome, 2007, vol. 18(12), pp. 880-886, 1 page, Abstract.

Jiang et al., "Significant associations of stearoyl-CoA desaturase (SCD1) gene with fat deposition and composition in skeletal muscle," Int'l J. Biol. Sci., 2008, vol. 4, pp. 345-351.
Lagziel et al., "Association Between SSCP Haplotypes at the Bovine Growth Hormone Gene and Milk Protein Percentage," Genetics 1996, vol. 142, pp. 945-951.
Lagziel et al., "DNA Sequence of SSCP Haplotypes at the Bovine Growth Hormone (bGH) gene," Animal Genetics 1999, vol. 30, pp. 362-365.
Leveau, "Candidate genes for beef quality—allele frequencies in Swedish beef cattle," 2008, retrieved from http://ex-epsilon.slu.se/2686/1/301_Carina_Leveau.pdf, retrieved on Jul. 12, 2016, pp. 1-48.
Li et al, "Analysis of Population Differentiation in North Eurasian Cattle (Bos taurus) Using Single Nucleotide Polymorphisms in Three Genes Associated with Production Traits," Animal Genetics, 2006, vol. 37, pp. 390-392.
Lo, "Clinical Applications of PCR, Introduction to the Polymerase Chain Reaction," Methods in Molecular Medicine, Humana Press Inc., 1998, vol. 16, 10 pages.
Lowe et al., "A computer program for selection of oligonucleotide primers for polymerase chain reactions," Nucleic Acids Research, 1990, vol. 18(7), pp. 1757-1761.
Perusse et al., The Human Obesity Gene Map: The 2004 Update, Obesity Research, 2005, vol. 13(3), pp, 381-490.
Rampazzo et al., A Deoxyribonucleotidase in Mitochondria: Involvement in Regulation of dNTP Pools and Possible Link to Genetic Disease, PNAS, 2000, vol, 97(15), pp. 8239-8244.
Rincker et al., "Relationship among GeneSTAR marbling marker, intramuscular fat deposition, and expected progeny differences in early weaned Simmental steers," J. Animal Sci., 2006, vol. 84, pp. 686-693.
Rozen et al., "Primer3 on the WWW for General Users and for Biologist Programmers," Methods in Molecular Biology, Bioinformatics Methods and Protocols, 2000, vol, 132, pp. 365-386.
Santalucia, "Physical Principles and Visual-OMP Software for Optimal PCR Design," Methods in Molecular Biology, Humana Press, 2007, vol. 402, pp. 3-33.
Surks et al., "Myosin Phosphatase-Rho Interacting Protein: A New Member of the Myosin Phosphatase Complex that Directly Binds RhoA," Journal of Biological Chemistry, vol. 275, No. 51, Dec. 2003, pp. 51484-51493.
Van Eenennaam et al., "Validation of commercial DNA tests for quantitative beef qualify traits," J. Animal Sci., 2007, vol. 85, pp. 891-900.
Viitala et al., "The Role of the Bovine Growth Hormone Receptor and Prolactin Receptor Genes in Milk, Fat and Protein Production in Finnish Ayrshire Dairy Cattle," Genetics, 2006, vol. 173, pp. 2151-2164.
Weiner et al., "Kits and their unique role in molecular biology: a brief retrospective," BioTechniques, vol. 44, Apr. 2008, pp. 701-704.
Williamson et al, "Genomic evolution in domestic cattle: Ancestral haplotypes and healthy beef," Genomics, 2011, vol, 97(5), pp. 304-312.
International Search Report for PCT/AU2010/001214 dated Feb. 11, 2011, 5 pages.
Preliminary Report on Patentability for PCT/AU2010/001214 dated Mar. 20, 2012, 8 pages.
Official Action for Australian Patent Application No. 2010295245, dated Aug. 27, 2015, 4 pages.
Extended Search Report for European Patent Application No. 10816481.5, dated Feb, 20, 2013, 8 pages.
Written Opinion for European Patent Application No. 10816481.5, dated Feb. 20, 2013, 6 pages.
Official Action for European Patent Application No. 10816481.5, dated Jul, 18, 2016, 6 pages.
Decision to Grant for European Patent Application No. 10816481.5, dated Nov. 9, 2017, 2 pages.
Official Action for Japanese Patent Application No. 2012-529066, dated Nov. 11, 2014, 5 pages, English translation.
Final Action for Japanese Patent Application No. 2012-529066, dated Nov. 10, 2015, 9 pages, English translation.

(56) References Cited

OTHER PUBLICATIONS

Notice of Acceptance for Japanese Patent Application No. 2012-529066, dated Jun. 30, 2016, 4 pages, English translation.
Official Action for U.S. Appl. No. 13/496,607, dated Dec. 2, 2013, 8 pages Restriction Requirement.
Official Action for U.S. Appl. No. 13/496,607, dated Mar. 24, 2014, 35 pages.
Final Action for U.S. Appl. No. 13/496,607, dated Oct. 6, 2014, 33 pages.
Notice of Allowance for U.S. Appl. No. 13/496,607, dated Jun. 30, 2015, 7 pages.
Official Action for U.S. Appl. No. 14/935,546, dated Aug. 16, 2017, 10 pages Restriction Requirement.
Official Action for U.S. Appl. No. 14/935,546, dated Feb. 23, 2018, 12 pages.

* cited by examiner

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 1
aggggtgctg agtctacagg        20

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 2
ctccaggagg caggagaag        19

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
ggaaggccag ttacatggca        20

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 4
cacaaccaag gccaaaatcg ca        22

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 5
agtaccagct gccctacca        19

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 6
ctgagacatg gagcgagcca        20

<210> SEQ ID NO 7
<211> LENGTH: 25
<212> TYPE: DNA
<213> ORGANISM: Artificial Sequence

```
<220> FEATURE:
<223> OTHER INFORMATION: Oligonucleotide primer

<400> SEQUENCE: 7
ccacaacgcc atcgagaaac gctac                                            25

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 8
ggccttccct gaccacccaa cttag                                            25

<210> SEQ ID NO 9
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 9
tctatgagaa gctgaaggac ctggaggaa                                        29

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10 cgggggtgc catcttccag                                                   20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11 cgggggtgc catcttccac                                                   20

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 12
atgaccctct ggtacgtctc cg                                               22

<210> SEQ ID NO 13
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 13
catgaccctc tggtacgtct cca                                              23
```

METHODS OF GENOTYPING LIVESTOCK

CROSS REFERENCE TO RELATED APPLICATION

This application is a continuation application of U.S. patent application Ser. No. 14/935,546, filed on Nov. 9, 2015, which is a divisional application of U.S. patent application Ser. No. 13/496,607, filed on Aug. 20, 2012, now U.S. Pat. No. 9,181,585, which issued on Nov. 10, 2015, which is a U.S. national phase patent application under 35 U.S.C. § 371 of International Patent Application No. PCT/AU2010/001214 entitled "Methods of Genotyping Livestock" filed Sep. 17, 2010, which claims benefit of priority of Australian Patent Application No. 2009904511 filed on Sep. 17, 2009. Each of these applications are hereby incorporated by reference in their entireties.

FIELD OF THE INVENTION

The present invention relates to methods of genotyping for selecting an animal with a desired trait such as the level of monounsaturated fats in muscle tissue, the types and/or ratio of different monounsaturated fats in muscle tissue, marbling, carcass weight, meat quality, speed of finishing, feedlot efficiency and/or consumer preference.

BACKGROUND OF THE INVENTION

It has been claimed that DNA testing can provide an indication of alleles associated with thyroglobulin gene polymorphism. However, Rincker et al. (2006) found the GeneSTAR marbling marker was not associated with intramuscular fat deposition in early weaned steers fed a high-concentrate diet and the thyroglobulin gene was not associated with other carcass, performance parameters, or marbling expected progeny difference. Similarly, Van Eenennaam et al. (2007) could not validate the utility of the markers.

By contrast, US 2008/0010696 shows that SCD SREB has relevance in marbling in Japanese cattle but not others. SREBP is a transcription factor which regulates gene expression levels of stearoyl-CoA desaturase (SCD1) and other genes relevant to lipid and fatty acid metabolism in tissue (Hoashi et al., 2007). The content of unsaturated fatty acid in beef is an important factor in taste and texture (Hoashi et al., 2007; EP 1845159) and the degree of marbling. A recent study revealed that the high SCD activities were positively correlated with beef marbling score, amount of monounsaturated fatty acid and conjugated linoleic acid, but negatively correlated with the amount of saturated fatty acid (Jiang et al., 2008).

U.S. Pat. No. 7,157,231 shows that bovine growth hormone (GH Exon 5) has an important role with the B & C alleles contributing to marbling, again this effect is confined to Japanese cattle. U.S. Pat. No. 7,238,479 shows that genetic testing for alleles of the gene encoding calcium activated neutral protease effecting meat tenderness in bovines is useful in selective breeding. US 2004/0261138 shows that genetic markers in the porcine melanocortin-4 receptor (MC4R) gene are associated with meat quality.

However, there is a need for further methods of genetic analysis for identifying livestock with desirable traits.

SUMMARY OF THE INVENTION

The present inventors have identified new polymorphic regions linked to desired traits.

In one aspect, the present invention provides a method of selecting an animal with a desired trait, the method comprising
  i) analysing the M-RIP, NT5M and/or TCAP genes of the animal for one or more polymorphisms associated with the desired trait, and
  ii) selecting an animal with one or more polymorphisms associated with the desired trait.

In a preferred embodiment, the one or more polymorphisms, more preferably a combination of polymorphisms, are characteristic of a haplotype associated with the desired trait.

In a further embodiment, step i) further comprises analysing the SREBP1 and/or GH genes, preferably at least the SREBP1 gene, of the animal for one or more polymorphisms associated with the desired trait.

In a preferred embodiment, the M-RIP gene is analysed by
  a) amplifying a region of the gene using an oligonucleotide primer comprising the sequence 5'-AGG GGT GCT GAG TCT ACA GG-3' (SEQ ID NO:1) and an oligonucleotide comprising the sequence 5'-CTC CAG GAG GCA GGA GAA G-3' (SEQ ID NO:2), or a variant of one or both primers which can be used to amplify the same region of the genome, and
  b) analysing the amplification products for the one or more polymorphisms.

In an embodiment, the M-RIP gene is analysed for an allele designated 10, 30, 40 or 60 as defined herein.

In another preferred embodiment, the NT5M gene is analysed by
  a) amplifying a region of the gene using an oligonucleotide primer comprising the sequence 5'-GGA AGG CCA GTT ACA TGG CA-3' (SEQ ID NO:3) and an oligonucleotide primer comprising the sequence 5'-CAC AAC CAA GGC CAA AAT CGC A-3' (SEQ ID NO:4), or a variant of one or both primers which can be used to amplify the same region of the genome, and
  b) analysing the amplification products for the one or more polymorphisms.

In an embodiment, the NT5M gene is analysed for an allele designated 10, 20 or 22 as defined herein.

In a further preferred embodiment, the TCAP gene is analysed by
  a) amplifying a region of the gene using an oligonucleotide primer comprising the sequence 5'-AGT ACC AGC TGC CCT ACC A-3' (SEQ ID NO:5) and an oligonucleotide primer comprising the sequence 5'-CTG AGA CAT GGA GCG AGC CA-3' (SEQ ID NO:6), or a variant of one or both primers which can be used to amplify the same region of the genome, and
  b) analysing the amplification products for the one or more polymorphisms.

In an embodiment, the TCAP gene is analysed for an allele designated 10 or 20 as defined herein.

In another preferred embodiment, the SREBP1 gene is analysed by
  a) amplifying a region of the gene using an oligonucleotide primer comprising the sequence 5'-CCA CAA CGC CAT CGA GAA ACG CTA C-3' (SEQ ID NO:7) and an oligonucleotide primer comprising the sequence 5'-GGC CTT CCC TGA CCA CCC AAC TTA G-3' (SEQ ID NO:8), or a variant of one or both primers which can be used to amplify the same region of the genome, and
  b) analysing the amplification products for the one or more polymorphisms.

In an embodiment, the SREBP1 gene is analysed for an allele designated S or L as defined herein and US 2008/0010696.

In an embodiment, the SREBP1 gene is analysed for an allele designated S or L as defined herein and US 2008/0010696.

In yet a further preferred embodiment, the GH gene is analysed by
a) amplifying a region of the gene using
1) an oligonucleotide primer comprising the sequence 5'-TCT ATG AGA AGC TGA AGG ACC TGG AGG AA-3' (SEQ ID NO:9) or a variant thereof which 20 can be used to amplify the same region of the genome, and
2) an oligonucleotide primer comprising the sequence 5'-CGG GGG GTG CCA TCT TCC AG-3' (SEQ ID NO:10) or an oligonucleotide primer comprising the sequence 5'-CGG GGG GTG CCA TCT TCC AC-3' (SEQ ID NO:11) or a variant of one or both primers which can be used to amplify the same region of the genome, and
3) an oligonucleotide primer comprising the sequence 5'-ATG ACC CTC TGG TAC GTC TCC G-3' (SEQ ID NO:12) or an oligonucleotide primer comprising the sequence 5'-CAT GAC CCT CTG GTA CGT CTC CA-3' (SEQ ID NO:13) or a variant of one or both primers which can be used to amplify the same region of the genome, and
b) analysing the amplification products for the one or more polymorphisms.

In an embodiment, the GH gene is analysed for an allele designated A, B, C or D as defined herein and U.S. Pat. No. 7,157,231.

In an embodiment, at least the M-RIP gene is analysed, more preferably at least the M-RIP and NT5M genes, at least the M-RIP and TCAP genes, at least the M-RIP, NT5M and TCAP genes, at least the SREBP1, M-RIP, NT5M and TCAP genes, at least the M-RIP, NT5M, TCAP and GH genes, or at least the SREBP1, M-RIP, NT5M, TCAP and GH genes. In alternate embodiments, at least the TCAP and GH genes, or at least the SREBP1 and NT5M genes, are analysed.

In an embodiment, the trait is the level of monounsaturated fats in muscle tissue, the types and/or ratio of different monounsaturated fats in muscle tissue, marbling, carcass weight, meat quality, speed of finishing, feedlot efficiency and/or consumer preference. In an embodiment, the meat quality trait is eye muscle area and/or tenderness.

Preferably, the animal is a livestock animal. More preferably, the livestock animal is a sheep, cow, pig, goat or horse. Even more preferably, the livestock animal is a cow.

In an embodiment, the cow is a Wagyu, the meat quality trait is eye muscle area (EMA) and the haplotypes (NT5M-MRIP-TCAP-GH) 22-40-20 B/C, 10-30-20 A, and 10-40-20-B/C, more preferably 22-40-20 B/C, are positively associated with higher EMA when compared to other NT5M-MRIP-TCAP-GH haplotypes. Furthermore, the haplotypes 20-30-20-A, 20-40-20-A and 22 40-10-B/C, more preferably 20-30-20-A and 20-40-20-A, are negatively associated with higher EMA when compared to other NT5M-MRIP-TCAP-GH haplotypes.

In a further embodiment, the cow is a Wagyu, the trait is carcass weight, and the haplotypes (TCAP-GH) 20-C, 10-C and 10-B, more preferably 20-C, are positively associated with higher carcass weight when compared to other TCAP-GH haplotypes.

In yet another embodiment, the cow is a Wagyu, the trait is marbling, and the haplotypes (MRIP-TCAP-GH) 30-10-B and 40-20-A are positively associated with higher marbling when compared to other MRIP-TCAP-GH haplotypes. Furthermore, the haplotypes 40-10-B, 40-10-A and 30-10-C are negatively associated with higher marbling when compared to other MRIP-TCAP-GH haplotypes.

In an embodiment, the 40.1 and 30.1 haplotypes of Table 2 are associated with the desired trait in cattle, preferably Wagyu, Simmental and/or Angus cattle.

In an embodiment, step i) is performed on a sample which comprises DNA that has been obtained from the animal.

In a further aspect, the present invention provides a method of breeding an animal with a desired trait, the method comprising selecting a first animal using a method of the invention, and crossing the first animal with a second animal of the same species but opposite sex.

In an embodiment, the second animal is also selected using a method of the invention.

In an embodiment of the above aspect, the sample is an egg, semen or an embryo. In relation to this embodiment, selection of an embryo can be used to accelerate the expansion or rare genotypes. Recovered embryo's can be stored, and preferred embryo's placed into a third party recipient animal such as a cow. The embryo's can also be split to speed up production of animals with the desired genotype.

In a further embodiment, the method comprises selecting a progeny of the cross for the desired trait using the method of the invention.

In another aspect, the present invention provides a method of genotyping an animal, the method comprising analysing the M-RIP, NT5M and/or TCAP genes of the animal for one or more polymorphisms.

This aspect of the invention can be used for a variety of purposes such as paternity testing, exclusion testing and breed composition testing.

With regard to the use of the above aspect for paternity testing, preferably the method comprises
i) genotyping an animal by analysing the M-RIP, NT5M and/or TCAP genes of the animal for one or more polymorphisms,
ii) determining the genotype of the candidate father and/or mother of the animal by analysing the M-RIP, NT5M and/or TCAP genes for the one or more polymorphisms, and
iii) comparing the genotypes from steps i) and ii) to determine the probability that the candidate father and/or mother is the parent of the animal.

As the skilled person would appreciate, steps i) and ii) can be performed in any order.

In an embodiment, the method further comprises analysing the SREBP1 and/or GH genes of the animal for one or more polymorphisms.

Preferably, the one or more polymorphisms, more preferably a combination of polymorphisms, are characteristic of a haplotype.

In yet a further aspect, the present invention provides an oligonucleotide primer for use in amplifying a polymorphic region of the M-RIP, NT5M and/or TCAP genes of an animal.

In an embodiment, the primer is selected from:
a) an oligonucleotide comprising a sequence selected from:

(SEQ ID NO: 1)
5'-AGG GGT GCT GAG TCT ACA GG-3', (SEQ ID NO: 2)
5'-CTC CAG GAG GCA GGA GAA G-3',

-continued

5'-GGA AGG CCA GTT ACA TGG CA-3', (SEQ ID NO: 3)

5'-CAC AAC CAA GGC CAA AAT CGC A-3', (SEQ ID NO: 4)

5'-AGT ACC AGC TGC CCT ACC A-3', (SEQ ID NO: 5)
and

5'-CTG AGA CAT GGA GCG AGC CA-3', (SEQ ID NO: 6)

b) an oligonucleotide comprising a sequence which is the reverse complement of any oligonucleotide provided in a), and c) a variant of a) or b) which can be used to amplify the same region of the animal genome as any one of the oligonucleotides of a) or b).

Also provided is a composition comprising an oligonucleotide of the invention and an acceptable carrier.

In a further aspect, the present invention provides a kit comprising an oligonucleotide of the invention.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIGS. 1 and 2 provide schematic representations of polymorphic markers on chromosome 19 used to define the 14 Mb haplotypes in cattle, with FIG. 1 providing a summary of the alleles analysed.

DETAILED DESCRIPTION OF THE INVENTION

General Techniques and Definitions

Figure 1:
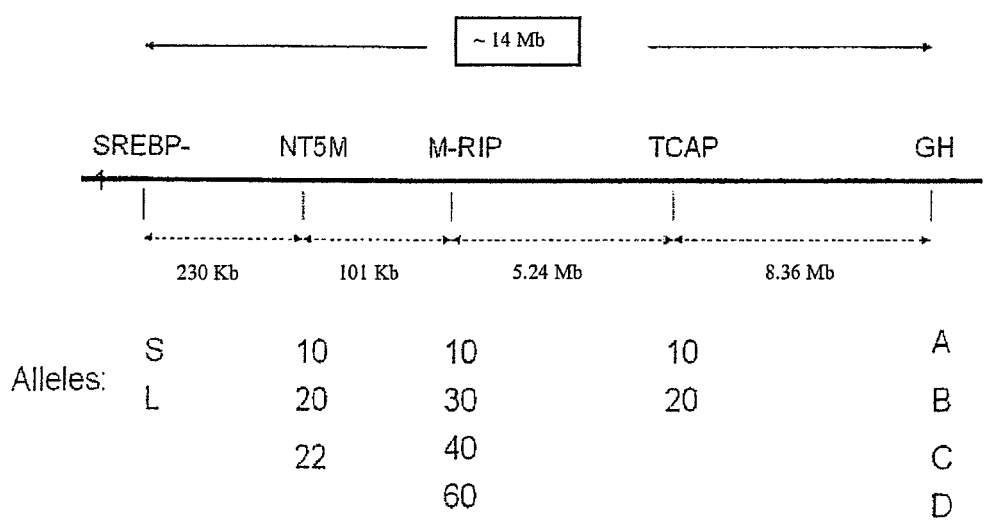

Unless specifically defined otherwise, all technical and scientific terms used herein shall be taken to have the same meaning as commonly understood by one of ordinary skill in the art (e.g., in cell culture, molecular genetics, animal breeding, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

A "haplotype" is the particular combination of alleles (sometimes identified by single nucleotide polymorphisms (SNPs)) on one chromosome or a part of a chromosome. Haplotypes can be exploited for the fine mapping of traits.

Some polymorphisms may be in linkage disequilibrium and are inherited in blocks. A "haplotype block" (also known in the art as a "frozen block") is thus a discrete chromosome region of high linkage disequilibrium (LD) and low haplotype diversity. It is expected that all pairs of polymorphisms within a block will be in strong linkage disequilibrium, whereas other pairs will show much weaker association. Blocks are hypothesized to be regions of low recombination flanked by recombination hotspots. Blocks may contain a large number of polymorphisms, but a few polymorphisms are enough to uniquely identify the haplotypes in a block.

An "ancestral haplotype" is passed from generation to generation just like familial haplotype blocks but is found at higher than expected frequencies in the population at large between animals not closely related, namely all arising from some distant ancestor. Generally, the phrases "haplotype" and "ancestral haplotype" are used herein interchangeably.

As used herein, the term "the one or more polymorphisms are characteristic of a haplotype" means that presence of the polymorphism(s), typically numerous polymorphisms, is a marker of a specific haplotype.

The term "polymorphism" refers to the coexistence of more than one form of a locus of interest. A region of the genome of which there are at least two different forms, i.e., two different nucleotide sequences, is referred to as a "polymorphic region" or "polymorphic locus". A polymorphic locus can be a single nucleotide, the identity of which differs in the other alleles. A polymorphic locus can also be more than one nucleotide long and/or can be a varying length due to insertions or deletions (such as of the number of repeats) at a given locus. The allelic form occurring most frequently in a selected population is often referred to as the reference and/or wild-type form. Other allelic forms are typically designated or alternative or variant alleles. Diploid organisms may be homozygous or heterozygous for allelic forms. A diallelic or biallelic polymorphism has two forms. A trialleleic polymorphism has three forms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $1/100$ or $1/1000$ members of a population). SNP usually arises due to substitution of one nucleotide for another at the polymorphic site. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site.

The terms "linkage", "linked" or variations thereof describe the tendency of genes, alleles, loci or genetic markers to be inherited together as a result of their location on the same chromosome. It can be measured by percent recombination between the two genes, alleles, loci, or genetic markers. The term "linkage disequilibrium" refers to a greater than random association between specific alleles at two marker loci within a particular population. In general, linkage disequilibrium decreases with an increase in physical distance. If linkage disequilibrium exists between two markers within one gene or block, then the genotypic information at one marker can be used to make probabilistic predictions about the genotype of the second marker.

Figure 2:
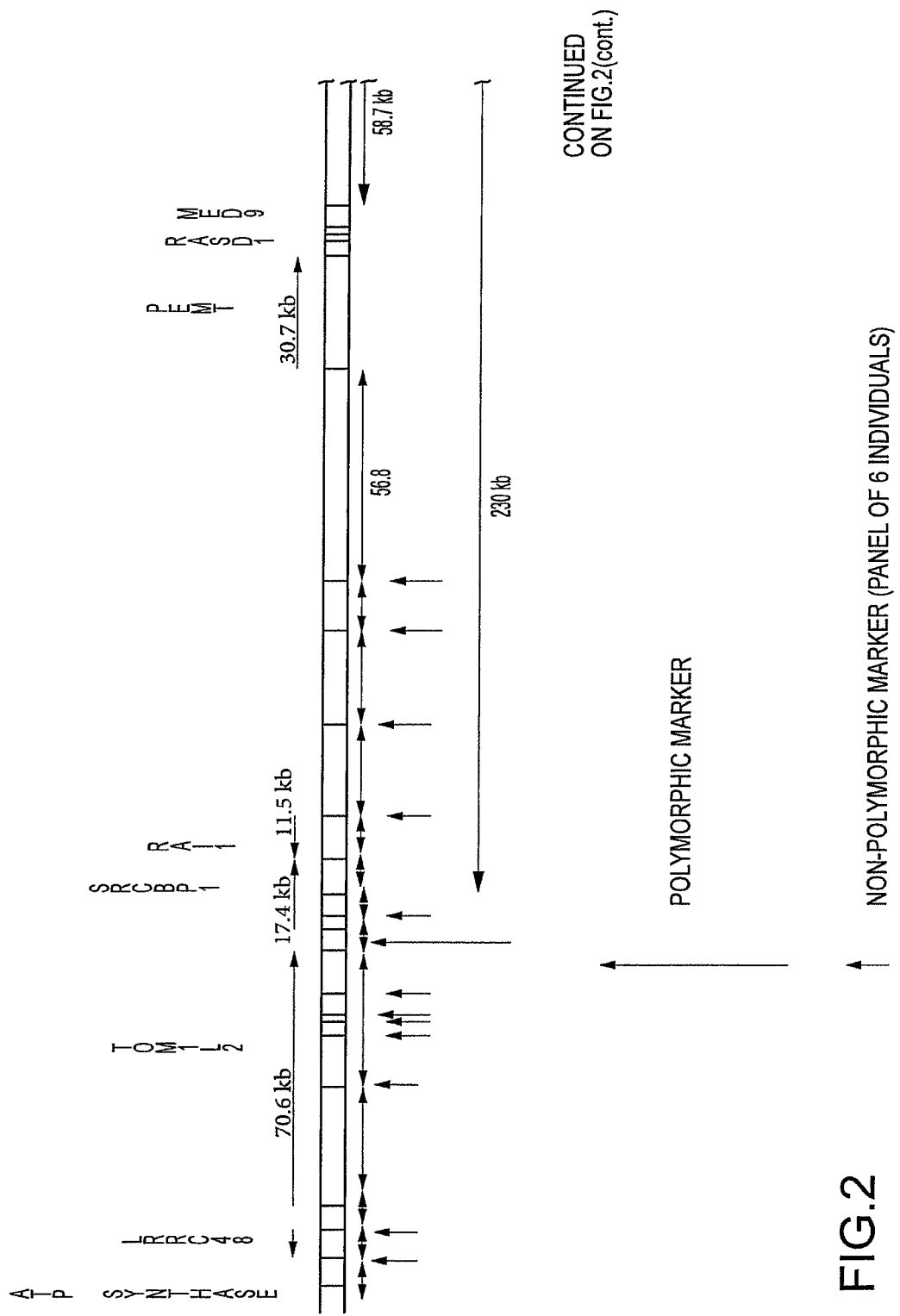
Figure 2:
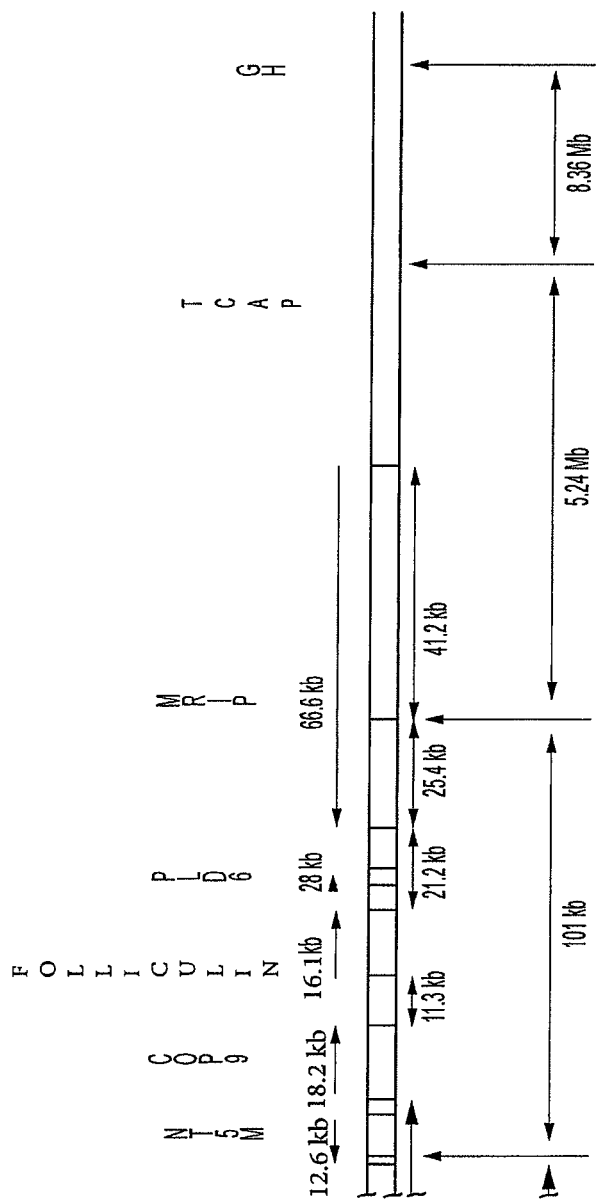

As used herein, the term "analyse" or variations thereof refers to determining the sequence, either directly (for example by actual sequencing) or indirectly (for example by the analysis of different fragment lengths following amplification and/or restriction enzyme cleavage), of polymorphic loci of the genes defined herein, particularly the specific alleles which have been disclosed (see, for example, FIGS. 1 and 2). Typically, a method of the invention will be conducted by analysing a sample obtained from the animal.

The "sample" refers to a material which comprises the animals genomic DNA, or RNA encoding a gene of interest. The sample can be used as obtained directly from the source or following at least one step to at least partially purify DNA or RNA from the sample obtained directly from the source. Preferably, the sample comprises genomic DNA. The sample can be prepared in any convenient medium which does not interfere with the methods of the invention. Typically, the sample is an aqueous solution or biological fluid as described in more detail below. The sample can be derived from any source, such as a physiological fluid, including blood, serum, plasma, saliva, sputum, ocular lens fluid, sweat, faeces urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, buccal swab, amniotic fluid, and the like. Herein, fluid homogenates of cellular tissues such as, for example, hair, skin and nail scrapings, meat extracts are also considered biological fluids. An important use of the invention is that it enables one skilled in the art to select rare alleles and haplotypes prior to expansion. Since these may be demonstrated by embryo biopsy it is possible to expand a very rare genotype. Thus, in a further embodiment the sample may be a biopsy from an embryo (preferably at the blastocyst stage), an egg or individual semen. Pretreatment may involve preparing plasma from blood, diluting viscous fluids, and the like. Methods of treatment can involve filtration, distillation, separation, concentration, inactivation of interfering components, and the addition of reagents. The selection and pretreatment of biological samples prior to testing is well known in the art and need not be described further.

As used herein, the term "gene" is to be taken in its broadest context and includes the deoxyribonucleotide sequences comprising the protein coding region of a structural gene and including sequences located adjacent to the coding region on both the 5' and 3' ends for a distance of about 1 kb on either end such that the gene corresponds to the length of the full-length mRNA. Regions further distances (than about 1 kb) from the coding region may also comprise part of a gene if they directly influence transcription. The sequences which are located 5' of the coding region and which are present on the mRNA are referred to as 5' non-translated sequences. The sequences which are located 3' or downstream of the coding region and which are present on the mRNA are referred to as 3' non-translated sequences. A genomic form or clone of a gene contains the coding region which is interrupted with non-coding sequences termed "introns" or "intervening regions" or "intervening sequences". Introns are segments of a gene which are transcribed into nuclear RNA (nRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "livestock animal" refers to any breed or population of animal kept by humans for a useful, commercial purpose. As used herein, a livestock animal can be mammal or avian. Generally, the livestock animal is an agricultural mammal, for example, bovine, equine, ovine, porcine. Livestock animals raised for the production of meat find use with the present invention, for example, beef cattle, pigs, goats, sheep, bison, chickens, turkeys, etc. The livestock animals can be in all stages of development, including embryonic, fetal, neonate, yearling, juvenile and adult stages.

The term "bovine", "cow", "cattle" or variations thereof refer to a domesticated (purebred or crossbreeds) or wild mammal that is a Bovinae, for example, of the genera *Bos* (e g, cattle or oxen) or Bison (e.g. American buffalo). Exemplary mammals of the genus *Bos* include without limitation *Bos taurus, Bos bovis, Bos frontalis* (gayal), *Bos gaurus* (gaur), *Bos grunniens* (domestic yak), *Bos grunniens×Bos taurus* (dzo), *Bos indicus* (zebu cattle), *Bos indicus gudali* (Gudali zebu), *Bos indicus×Bos taurus* (hybrid cattle), *Bos javanicus* (banteng), *Bos primigenius* (aurochs), and *Bos sauveli* (kouprey). *Bos* species for the production of meat products, for example beef cattle, which are of particular relevance to the invention include, but not necessarily limited to, Black Angus, Red Angus, Horned Hereford, Polled Hereford, Murray Gray, Charolais, Simmental, Limousine, Chianina, Brahman, Santa Gertrudis, Texas Longhorn and Wagyu. Exemplary dairy cattle breeds of *Bos* include without limitation Ayrshire, Brown Swiss, Canadiennem, Dutch Belted, Guernsey, Holstein (Holstein-Friesian), Jersey, Kerry, Milking Devon, Milking Shorthorn and Norwegian Red.

Polymorphisms and Haplotypes

The present inventors have shown that alleles of the M-RIP, NT5M and/or TCAP genes, particularly combinations thereof which may also include alleles of the SREBP1 and/or GH genes, represent ancestral haplotypes which can be used for selecting and/or genotyping animals.

As used herein, the term "M-RIP" refers to the Myosin Phosphatase-Rho interacting protein encoding gene, the term "SREBP-1" refers to the Sterol Regulatory Element Binding Protein-1 encoding gene (an example of the cow SREBP-1 gene is described in US 2008/0010696), the term "GH" refers to the Growth Hormone encoding gene (an example of the cow GH gene is described in U.S. Pat. No. 7,157,231), the term "NT5M" refers to the 5',3'-Nucleotidase, Mitochondrial encoding gene, and the term "TCAP" refers to the titin-cap (telethonin) encoding gene. The location of these genes in the cow genome on chromosome 19 is shown in FIGS. 1 and 2.

As outlined in FIG. 1, in cattle there are at least two informative alleles of the SREBP-1 gene (designated S and L), at least three informative alleles of the NT5M gene (designated 10, 20 and 22), at least four informative alleles of the M-RIP gene (designated 10, 30, 40 and 60), at least two informative alleles of the TCAP gene (designated 10 and 20), and at least four informative alleles of the GH gene (designated A, B, C and D). Of all possible combinations of these alleles, 41 have been identified thus far in cattle with varying degrees of representation between different breeds.

When referring to the specific haplotypes, when all 5 genes are analysed the same order is used (SREBP1-NT5M-MRIP-TCAP-GH) as the genes exist on the cow genome. Thus, L-20-30-20-A means the animal has the L allele of SREBP1, the 20 allele of NT5M, the 30 allele of M-RIP, the 20 allele of TCAP and the A allele of GH.

As used herein, the L and S designations for SREBP1 correspond to the same nomenclature used in US 2008/0010696. More specifically, "L" refers to the larger (428-432 bp) fragment, and "S" refers to the smaller (343-346 bp) fragment, following amplification with primers comprising the sequence 5'-CCA CAA CGC CAT CGA GAA ACG CTA C-3' (SEQ ID NO:7) and 5'-GGC CTT CCC TGA CCA CCC AAC TTA G-3' (SEQ ID NO:8).

As used herein, the 10, 20 and 22 designations for NT5M correspond to the 321 bp, 331 bp and 334 bp, respectively, products following amplification with primers comprising the sequence 5'-GGA AGG CCA GTT ACA TGG CA-3' (SEQ ID NO:3) and 5'-CAC AAC CAA GGC CAA AAT CGC A-3' (SEQ ID NO:4).

As used herein, the 10, 30, 40 and 60 designations for M-RIP correspond to the 192.about.193 bp, 201.about.203 bp, 208.about.209 bp, 218.about.220 bp, respectively, products following amplification with primers comprising the sequence 5'-AGG GGT GCT GAG TCT ACA GG-3' (SEQ ID NO:1) and 5'-CTC CAG GAG GCA GGA GAA G-3' (SEQ ID NO:2).

As used herein, the 10 and 20 designations for TCAP correspond to the smaller (approximately .about.230.about.235 bp) and the larger (about 245 bp), respectively, products following amplification with primers comprising the sequence 5'-AGT ACC AGC TGC CCT ACC A-3' (SEQ ID NO:5) and sequence 5'-CTG AGA CAT GGA GCG AGC CA-3' (SEQ ID NO:6).

As used herein, the A, B and C designations for GH correspond to the same nomenclature used in U.S. Pat. No. 7,157,231. The D designation is defined as in the Examples herein. These designation and the corresponding genotypes are summarized in Table 4, and relate to various combinations of polymorphisms in the codons encoding amino acids 127 and 172 of the GH protein.

Oligonucleotide Primers

As those skilled in the art would be aware, the sequence of the oligonucleotide primers described herein can be varied to some degree without effecting their usefulness for the methods of the invention. A "variant" of an oligonucleotide disclosed herein (also referred to herein as a "primer" or "probe" depending on its use) useful for the methods of the invention includes molecules of varying sizes of, and/or are capable of hybridising to the genome close to that of, the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise the target region. In addition, variants may readily be designed which hybridise close (for example, but not limited to, within 50 nucleotides or within 100 nucleotides) to the region of the genome where the specific oligonucleotides defined herein hybridise. Oligonucleotides can be naturally occurring or synthetic, but are typically prepared by synthetic means.

The term "primer" as used herein, is meant to encompass any nucleic acid that is capable of priming the synthesis of a nascent nucleic acid in a template-dependent process. Primers may be provided in double-stranded or single-stranded form, although the single-stranded form is preferred. Primers act as a point of initiation of template-directed DNA synthesis under appropriate conditions (e.g., in the presence of four different nucleoside triphosphates and as agent for polymerization, such as DNA or RNA polymerase or reverse transcriptase) in an appropriate buffer and at a suitable temperature. Methods of primer design are well-known in the art, based on the design of complementary sequences obtained from standard Watson-Crick base-pairing (i.e., binding of adenine to thymine or uracil and binding of guanine to cytosine). A primer need not match the exact sequence of a template, but must be sufficiently complementary to hybridize with the template. Computerized programs, when provided with suitable information regarding a target region, for selection and design of amplification primers are available from commercial and/or public sources well known to the skilled artisan. The length of a primer may vary but typically ranges from 15 to 30 nucleotides.

Primers used in the methods of the invention can have one or more modified nucleotides. Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well.

Chimeric primers can also be used. Chimeric primers are primers having at least two types of nucleotides, such as both deoxyribonucleotides and ribonucleotides, ribonucleotides and modified nucleotides, two or more types of modified nucleotides, deoxyribonucleotides and two or more different types of modified nucleotides, ribonucleotides and two or more different types of modified nucleotides, or deoxyribonucleotides, ribonucleotides and two or more different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. Other forms of chimeric primers are, for example, 5'-(2'-O-Methyl) RNA-RNA-3' or 5'-(2'O-Methyl) RNA-DNA-3'.

The term "primer pair" refers to a set of primers including an upstream primer that hybridizes with the 3' end of the complement of the nucleic acid to be amplified and a downstream primer that hybridizes with the 3' end of the sequence to be amplified as different purine or pyrimidine bases. Such modifications are well known in the art.

Primers may be chemically synthesized by methods well known within the art. Chemical synthesis methods allow for the placement of detectable labels such as fluorescent labels, radioactive labels, etc. to be placed virtually anywhere within the sequence. Solid phase methods as well as other methods of oligonucleotide or polynucleotide synthesis known to one of ordinary skill may used within the context of the disclosure.

Genetic Screening

Genetic assay methods useful for the invention include, but are not limited to, sequencing of the DNA at one or more of the relevant positions; differential hybridisation of an oligonucleotide probe designed to hybridise at the relevant positions of the desired sequence; denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; selective DNA amplification using oligonucleotides which are matched for one sequence and unmatched for a polymorphism thereof or vice versa; or the selective introduction of a restriction site using a PCR (or similar) primer matched for alleles of a polymorphic locus, followed by a restriction digest. As indicated above, the assay may be indirect, i.e. capable of detecting a polymorphism at another position or gene which is known to be linked to a polymorphism of the interest. The probes and primers may be fragments of DNA isolated from nature or may be synthetic.

Nucleic acid amplification can be performed using any technique known in the art such as, but not limited to, polymerase chain reaction (PCR), strand displacement amplification (SDA), nucleic acid sequence based amplification (NASBA), rolling circle amplification (RCA), T7 polymerase mediated amplification, T3 polymerase mediated amplification and SP6 polymerase mediated amplification.

In one method, a primer pair are used which hybridise to one allele but not another, for instance as described for the GH gene in U.S. Pat. No. 7,157,231. Whether amplified DNA is produced will then indicate which allele is present.

Another method employs similar primer pairs but, as well as hybridising to only one of the alleles, they introduce a restriction site which is not otherwise there in any known allele.

In an alternative method, following amplification the products are sequenced. Preferably the products are sequenced without subcloning such that if two different alleles are present in the individual being tested their presence can easily be identified. If the products are subcloned a suitable number of subclones would need to be sequenced to ensure that both alleles have been analysed.

In order to facilitate subsequent cloning of amplified sequences, primers may have restriction enzyme sites appended to their 5' ends. Thus, all nucleotides of the oligonucleotide primers are derived from the gene sequence of interest or sequences adjacent to that gene except the few nucleotides necessary to form a restriction enzyme site. Such enzymes and sites are well known in the art. The primers themselves can be synthesized using techniques which are well known in the art. Generally, the primers can be made using synthesizing machines which are commercially available.

A non-denaturing gel may be used to detect differing lengths of fragments resulting from digestion with an appropriate restriction enzyme. The DNA is usually amplified before digestion, for example using the polymerase chain reaction (PCR) method and modifications thereof.

PCR techniques that utilize fluorescent dyes may also be used to detect the genetic locus of interest. These include, but are not limited to, the following five techniques.

i) Fluorescent dyes can be used to detect specific PCR amplified double stranded DNA product (e.g. ethidium bromide, or SYBR Green I).

ii) The 5' nuclease (TaqMan) assay can be used which utilizes a specially constructed primer whose fluorescence is quenched until it is released by the nuclease activity of the Taq DNA polymerase during extension of the PCR product.

iii) Assays based on Molecular Beacon technology can be used which rely on a specially constructed oligonucleotide that when self-hybridized quenches fluorescence (fluorescent dye and quencher molecule are adjacent). Upon hybridization to a specific amplified PCR product, fluorescence is increased due to separation of the quencher from the fluorescent molecule.

iv) Assays based on Amplifluor (Intergen) technology can be used which utilize specially prepared primers, where again fluorescence is quenched due to self-hybridization. In this case, fluorescence is released during PCR amplification by extension through the primer sequence, which results in the separation of fluorescent and quencher molecules.

v) Assays that rely on an increase in fluorescence resonance energy transfer can be used which utilize two specially designed adjacent primers, which have different fluorochromes on their ends. When these primers anneal to a specific PCR amplified product, the two fluorochromes are brought together. The excitation of one fluorochrome results in an increase in fluorescence of the other fluorochrome. Such assays may also use a ligase so that the two annealed primers joined together.

In a particularly useful embodiment, two or more amplification reactions are performed in a single vessel, known in the art as multiplexing. For instance, alleles described herein in the SREBP1, NT5M, M-RIP, TCAP and GH genes can be analysed in a single reaction.

The one or more polymorphisms of the SREBP1 gene can be analysed as described in US 2008/0010696. Furthermore, the one or more polymorphisms of the GH gene can be analysed as described in U.S. Pat. No. 7,157,231, however, alternatives such as sequence specific priming (SSP) can be used.

EXAMPLES

Example 1—Identification and Analysis of Haplotypes

The cattle genomic region shown in FIGS. 1 and 2 was interrogated by an entwinement algorithm which revealed a highly polymorphic locus designated M-RIP. When combined with adjacent polymorphisms, SREBP1, NT5M, T-CAP and/or GH ancestral haplotypes were identified.

Primers useful in the methods of the invention for amplifying polymorphic regions of the M-RIP, NT5M and TCAP genes, as well as the SREBP1 and GH genes, are listed in Table 1. Depending on the individual, amplification products for the NT5M gene are between about 320 and about 340 bp, for the M-RIP gene between about 190 and about 250 bp, and for the TCAP gene between about 230 and about 250 bp.

TABLE 1

Primers useful for the invention.

| Gene | Primers |
|---|---|
| SREBP1 | CCA CAA CGC CAT CGA GAA ACG CTA C (SEQ ID NO: 7) |

TABLE 1-continued

Primers useful for the invention.

| Gene | Primers |
|---|---|
| | GGC CTT CCC TGA CCA CCC AAC TTA G (SEQ ID NO: 8) |
| NT5M | GGA AGG CCA GTT ACA TGG CA (SEQ ID NO: 3) |
| | CAC AAC CAA GGC CAA AAT CGC A (SEQ ID NO: 4) |
| M-RIP | AGG GGT GCT GAG TCT ACA GG (SEQ ID NO: 1) |
| | CTC CAG GAG GCA GGA GAA G (SEQ ID NO: 2) |
| TCAP | AGT ACC AGC TGC CCT ACC A (SEQ ID NO: 5) |
| | CTG AGA CAT GGA GCG AGC CA (SEQ ID NO: 6) |
| GH | TCT ATG AGA AGC TGA AGG ACC TGG AGG AA (SEQ ID NO: 9) |
| | CGG GGG GTG CCA TCT TCC AG (SEQ ID NO: 10) |
| | CGG GGG GTG CCA TCT TCC AC (SEQ ID NO: 11) |
| | ATG ACC CTC TGG TAC GTC TCC G (SEQ ID NO: 12) |
| | ATG ACC CTC TGG TAC GTC TCC A (SEQ ID NO: 13) |

Figure 3:
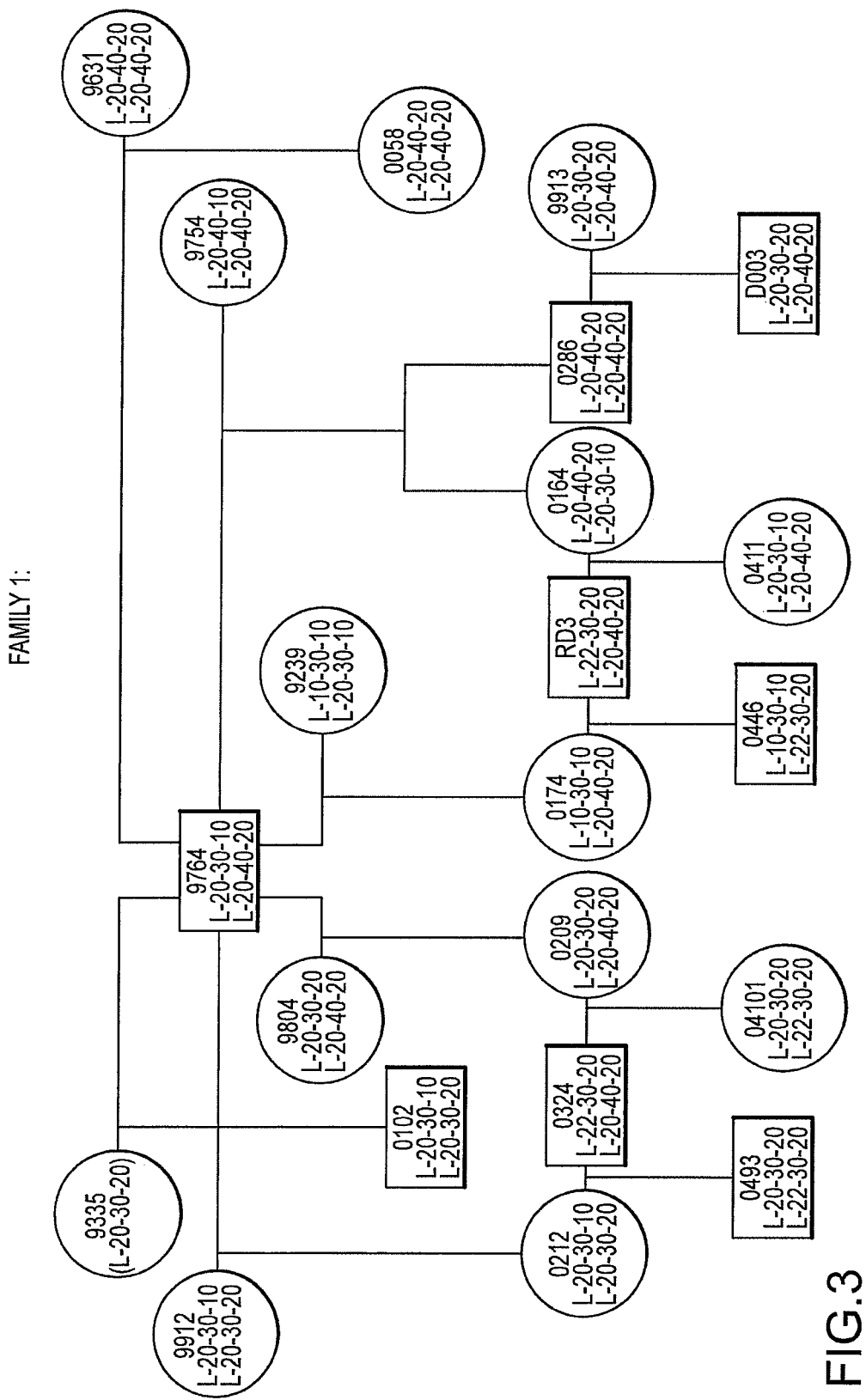
FIG. 3 shows the stable inheritance of the haplotypes of the invention in three different families of cattle.
Figure 3:
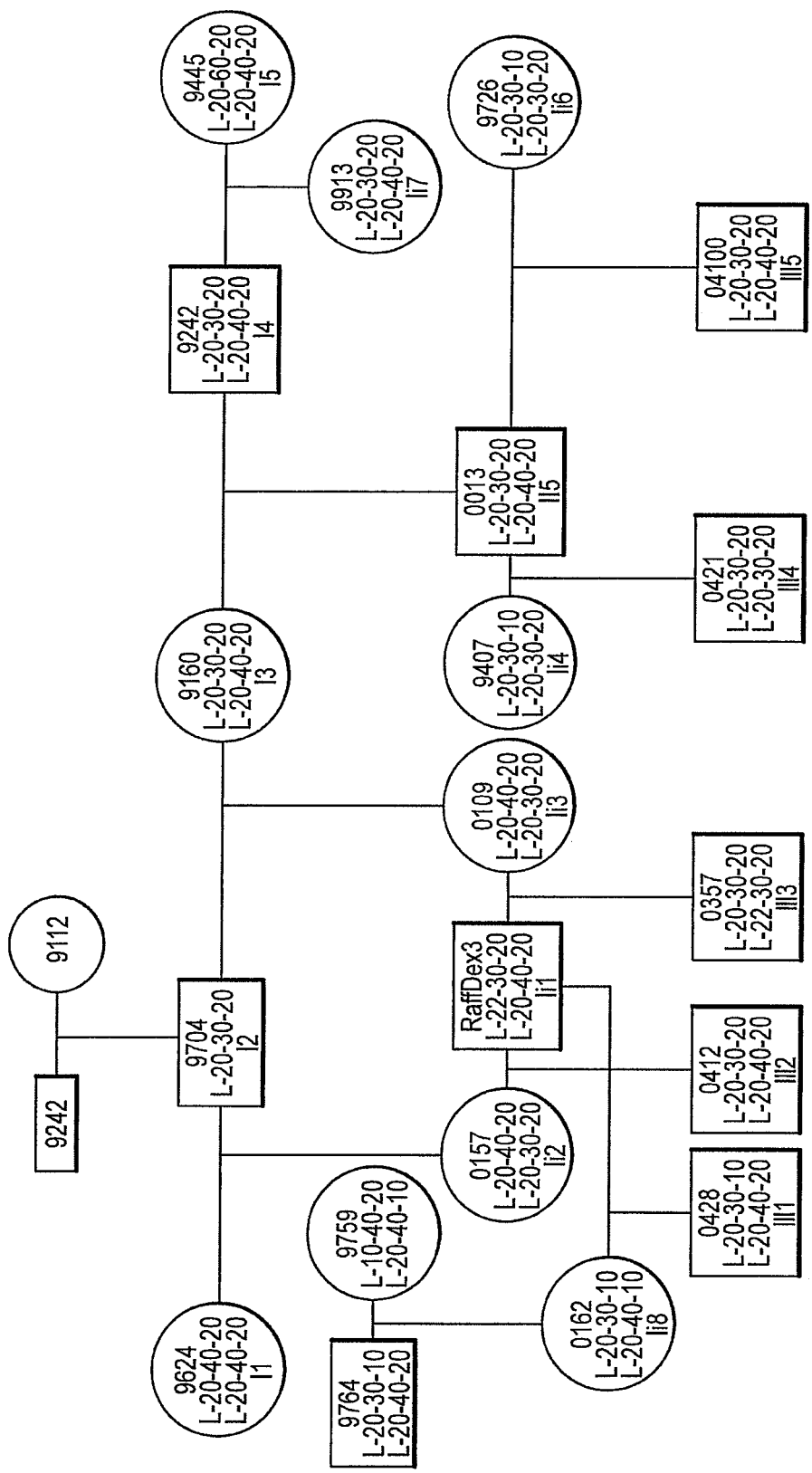
Figure 3:
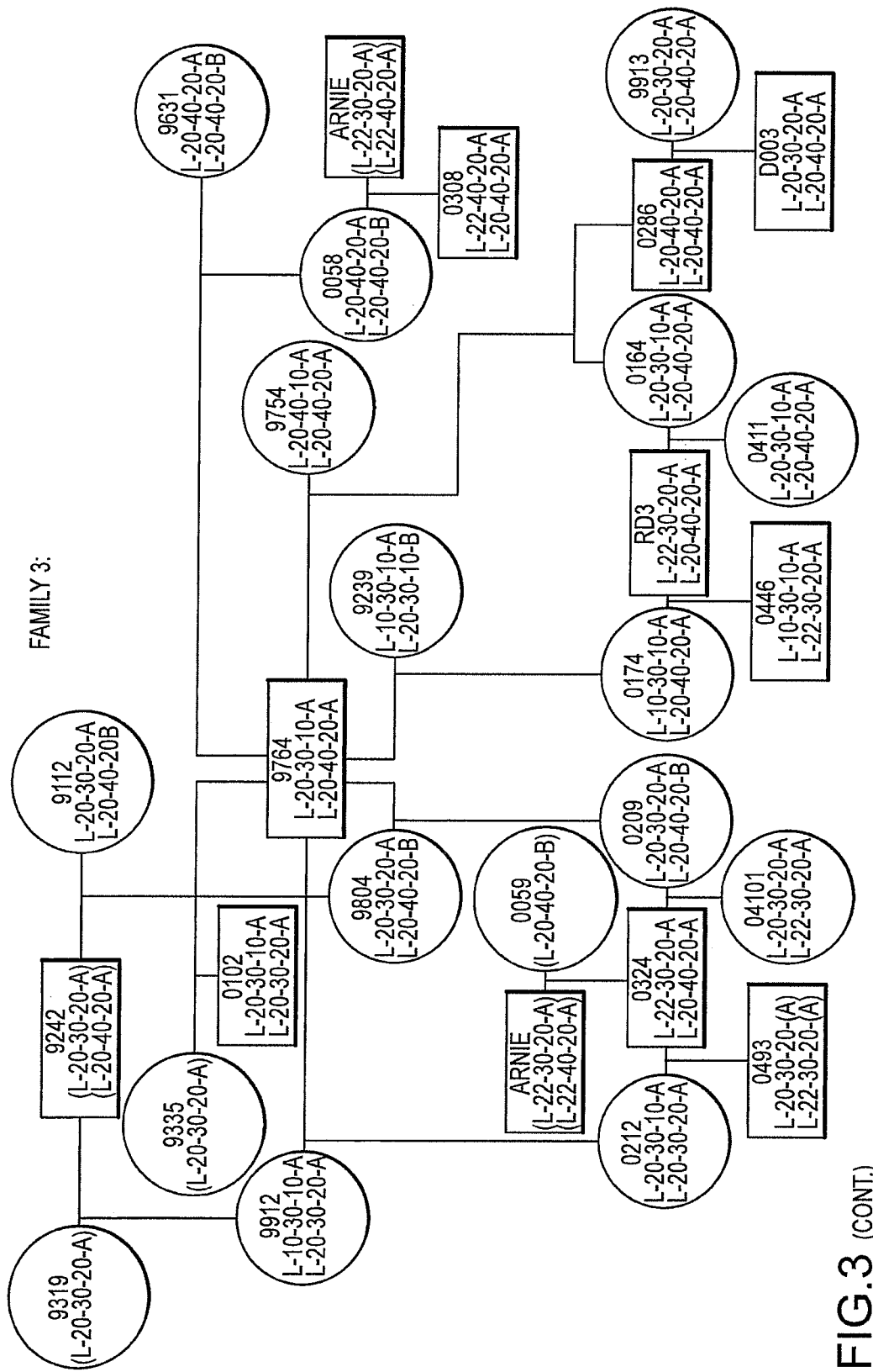

The specific ancestral haplotypes which were identified are listed in Tables 2 and 3. These haplotypes have been confirmed by family analysis as shown in FIG. 3.

TABLE 2

Ancestral haplotypes - SREBP1 to TCAP

| 10.1 | L-20-10-10 | 60.1 | S-10-60-10 |
| 10.2 | L-20-10-20 | 60.2 | L-20-60-20 |
| 10.3 | L-10-10-20 | 60.3 | S-10-60-20 |
| 10.4 | L-10-10-10 | 60.4 | S-20-60-10 |
| 30.1 | L-22-30-20 | 40.1 | L-22-40-20 |
| 30.2 | L-20-30-20 | 40.2 | L-20-40-20 |
| 30.3 | L-20-30-10 | 40.3 | L-20-40-10 |
| 30.1 | S-20-30-20 | 40.4 | L-20-40-20 |
| 30.5 | L-10-30-10 | 40.5 | L-10-40-10 |
| 30.6 | L-10-30-20 | 40.6 | L-10-40-20 |
| 30.7 | S-20-30-10 | 40.7 | S-20-40-10 |
| 30.8 | L-22-30-10 | 40.8 | L-22-40-10 |
| 30.9 | S-10-30-20 | 40.9 | S-10-40-20 |

TABLE 3 allele frequirencies (%) of ancestrial haplotypes - SREBP1 to TCAP

| | SREB | | NT5M | | | M-RIP | | | | TCAP | | GH | | | |
|---|---|---|---|---|---|---|---|---|---|---|---|---|---|---|---|
| | S | L | 10 | 20 | 22 | 10 | 30 | 40 | 60 | 10 | 20 | A | B | C | n |
| Jersey | 5 | 96 | 23 | 64 | 14 | 36 | 23 | 23 | 18 | 0 | 100 | 60* | 40* | 0* | 11 6* |
| Simm | 7 | 93 | 11 | 88 | 2 | 0 | 43 | 50 | 7 | 22 | 78 | 77 | 23 | 0 | 274 |
| Angus | 1 | 99 | 13 | 71 | 16 | 0 | 51 | 42 | 7 | 28 | 72 | 87 | 14 | 0 | 52 |
| Wagyu | 26 | 74 | 20 | 69 | 11 | 13 | 44 | 17 | 26 | 59 | 41 | 67 | 20 | 13 | 27 |

With regard to Table 2, the numbers 10.1, 60.1 etc correspond to specific haplotypes. The L and S designations correspond to the same nomenclature used in US 2008/0010696. The numbers next to L or S correspond to specific amplification products from the NT5M gene. The next numbers correspond to specific amplification products from the M-RIP gene. The next numbers in the series (for example L-20-10-10) correspond to specific amplification products from the TCAP gene. Finally, when present the next character in the series (for example, A, B, C or D) corresponds to specific amplification products from the GH gene.

Figure 4:
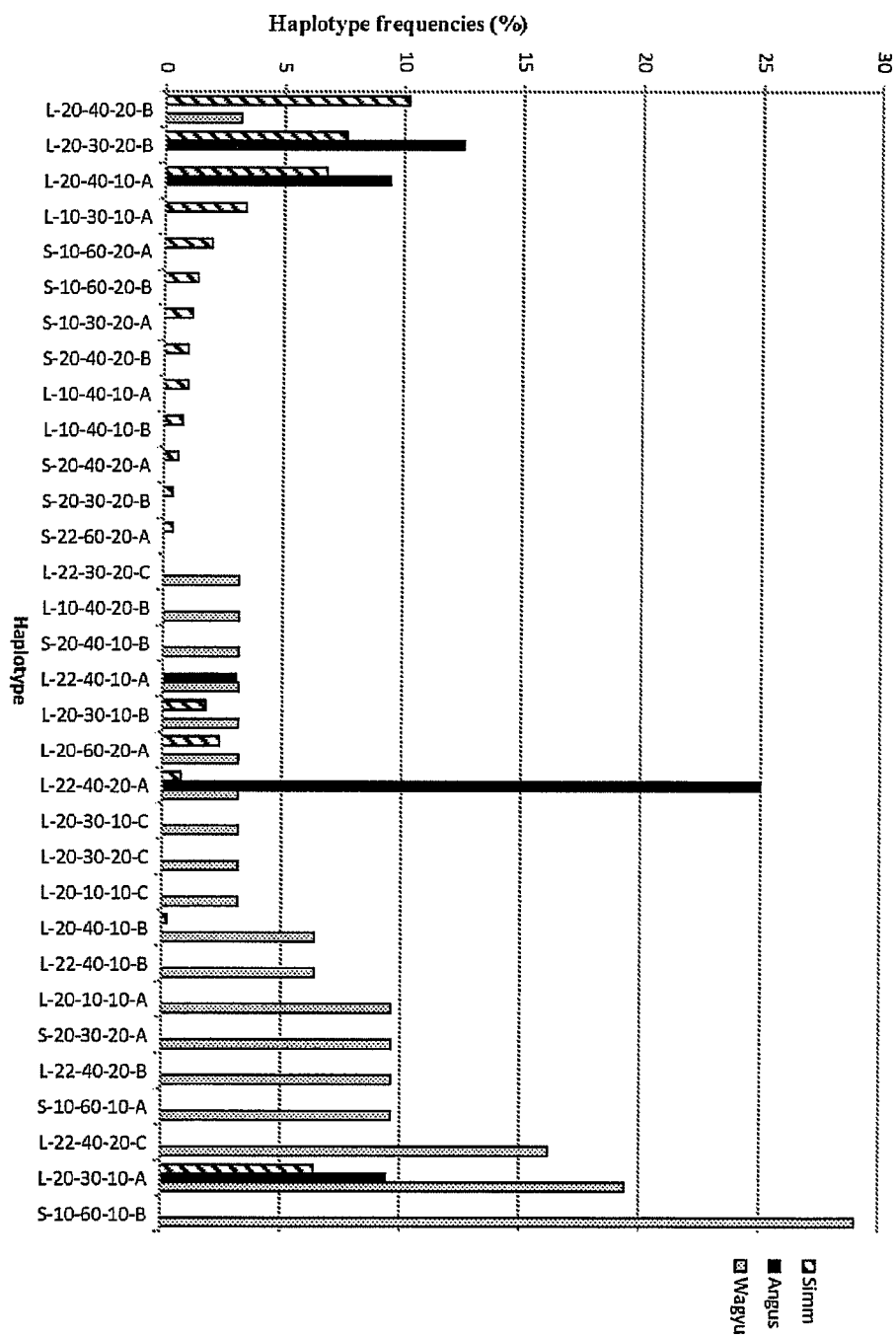
FIG. 4 shows the amplification products of the M-RIP gene using the primers provided in Table 1.

SREBP1 marker, bands at 343-346 bp and 428-432 bp represent short (S) and long (L), respectively. NT5M marker, bands at 321 bp, 331 bp and 334 bp are designated 10, 20 and 22 respectively. M-RIP, bands at 192-193 bp, 201-203 bp, 208-209 bp, 210-212 bp, 218-220 bp, 226-227 bp and 231 are designated 10, 30, 40, 50, 60, 80 and 90 respectively. When analysing genotypes at the GH loci a fourth haplotype was identified which is not described in U.S. Pat. No. 7,157,231. This haplotype was designated D (Table 4). Guidance as to the relative size of each amplification product for the M-RIP gene is provided in FIG. 4. Generally, the lower the number the smaller the amplification product.

TABLE 4

Genotypes of GHex5.

| Genotype | 127 | 172 |
|---|---|---|
| A | CTG | ACG |
| B | GTG | ACG |
| C | GTG | ATG |
| D | CTG | ATG |

Figure 5:
FIG. 5 shows SREBP1 to GH haplotype frequencies in different breeds (Simm=Simmental, AA=Angus).

A total of 41 different haplotypes were observed for the 5 genes analysed (Table 5 and FIG. 5). Table 5 does not include the 6 haplotypes that occurred only once in the 298 cattle (152 Simmental, 31 Wagyu and 16 Angus) analysed. Two haplotypes are common in around 20% of the cattle tested. 35 of the haplotypes show different frequencies in different breeds. Analysis of SREBP1, NT5M, M-RIP, T-CAP and GH was found to be more informative than SREBP1 and GH alone. The frequency of different haplotypes in Simmental cattle is summarized in Table 6.

TABLE 5

Combined frequirencies of observed haplotypes.

| SREB | NT5M | M-RIP | TCAP | GH | Freq. % |
|---|---|---|---|---|---|
| L | 20 | 30 | 20 | A | 18.6* |
| L | 20 | 40 | 20 | A | 14.7* |
| L | 20 | 30 | 10 | A | 9.7 |

TABLE 5-continued

Combined frequirencies of observed haplotypes.

| SREB | NT5M | M-RIP | TCAP | GH | Freq. % |
|---|---|---|---|---|---|
| L | 22 | 40 | 20 | A | 7.4 |
| S | 10 | 60 | 10 | B | 7.1 |
| L | 20 | 30 | 20 | B | 5.0 |
| L | 20 | 40 | 10 | A | 4.1 |
| L | 22 | 40 | 20 | C | 3.5 |
| L | 20 | 40 | 20 | B | 3.3 |
| L | 20 | 10 | 10 | A | 2.9 |
| S | 10 | 60 | 10 | A | 2.9 |
| L | 22 | 40 | 20 | B | 2.6 |
| S | 20 | 30 | 20 | A | 2.1 |
| L | 20 | 60 | 20 | A | 1.6 |
| L | 22 | 40 | 10 | A | 1.5 |
| L | 20 | 40 | 10 | A | 1.5 |
| L | 20 | 40 | 20 | C | 1.5 |
| L | 22 | 40 | 10 | B | 1.4 |
| L | 20 | 30 | 10 | B | 1.2 |
| L | 20 | 10 | 10 | C | 1.0 |
| L | 20 | 30 | 10 | C | 1.0 |
| L | 10 | 30 | 10 | A | 0.9 |
| L | 20 | 30 | 20 | C | 0.7 |
| L | 22 | 30 | 20 | C | 0.7 |
| L | 10 | 40 | 20 | B | 0.7 |
| S | 20 | 40 | 10 | B | 0.7 |
| S | 10 | 60 | 20 | A | 0.5 |
| S | 10 | 60 | 20 | B | 0.4 |
| S | 10 | 30 | 20 | A | 0.3 |
| S | 20 | 40 | 20 | B | 0.3 |
| L | 10 | 40 | 10 | A | 0.3 |
| L | 10 | 40 | 10 | B | 0.2 |
| S | 20 | 40 | 20 | A | 0.2 |
| S | 20 | 30 | 20 | B | 0.1 |
| S | 22 | 60 | 20 | A | 0.1 |

TABLE 6

Simmental haplotype frequencies.

| Haplotype ID | SREBP | NT5M | M-RIP | T-CAP | GH | Frequency |
|---|---|---|---|---|---|---|
| 30.2.3 | L | 20 | 30 | 20 | A | 22.7.8% |
| 30.2.2 | L | 20 | 30 | 20 | B | 7.8% |
| 30.3.3 | L | 20 | 30 | 10 | A | 6.8% |
| 30.3.2 | L | 20 | 30 | 10 | B | 1.7% |
| 30.5.3 | L | 10 | 30 | 10 | A | 3.4% |
| 30.6.3 | L | 10 | 30 | 20 | A | 0.4% |
| 30.9.3 | S | 10 | 30 | 20 | A | 0.8% |
| 30.4.2 | S | 20 | 30 | 20 | B | 0.4% |
| 40.2.3 | L | 20 | 40 | 20 | A | 28.2% |
| 40.2.2 | L | 20 | 40 | 20 | B | 9.1% |
| 40.3.3 | L | 20 | 40 | 10 | A | 7.2% |
| 40.1.3 | L | 22 | 40 | 20 | A | 0.8% |
| 40.4.2 | S | 20 | 40 | 20 | B | 1.1% |
| 40.5.3 | L | 10 | 40 | 10 | A | 1.1% |
| 40.5.2 | L | 10 | 40 | 10 | B | 0.8% |
| 60.2.3 | L | 20 | 60 | 20 | A | 2.3% |
| 60.3.2 | S | 10 | 60 | 20 | B | 1.3% |
| 60.3.3 | S | 10 | 60 | 20 | A | 1.9% |
| 60.7.3 | S | 22 | 60 | 20 | A | 0.4% |

Example 2—Haplotypes and Production Traits in Wagyu

The Japanese Black cattle breed "Wagyu" is the industry bench mark for high marbling (intramuscular fat) and thus taste. Within Wagyu phenotypic traits were assessed on carcasses from the Australian Cattle Company (AACo). Statistical analysis of data obtained from approximately 67 Wagyu showed significant, or near significant, correlation signals with combinations of NT5M to GH alleles in the SREBP-GH region on bovine Chromosome 19.

The SREB locus alleles (S/L) were found not to be relevant in this context as Wagyu animals usually have the characteristic S allele and are all high marbling.

Figure 6:
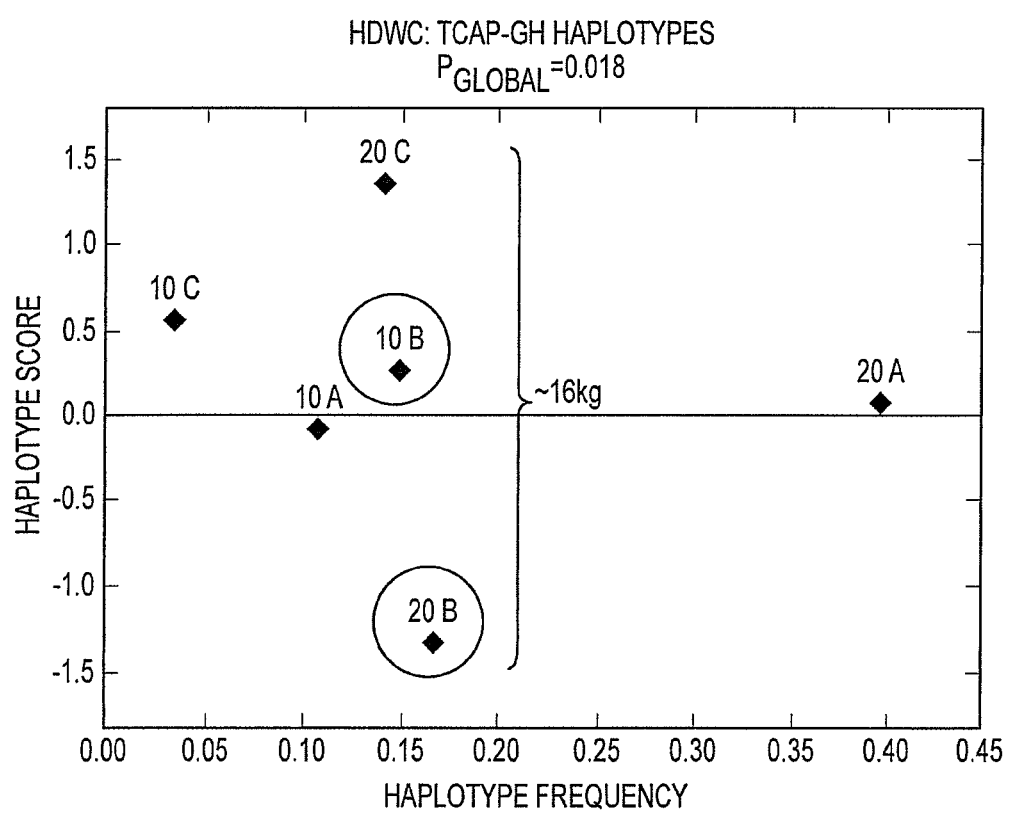
FIG. 6 shows the correlation between TCAP-GH haplotypes and hot dead carcass weight.

The hot dead carcass weight (HDCW) is associated as expected with alleles in the growth hormone locus (GH)—positive for the GH C allele and negative for the B allele. When additionally looking at TCAP alleles further useful information could be obtained from the genetic analysis, with the TCAP 10 and 20 alleles segregating with low carcass weight for the 20-B haplotype and improved carcass weight for the 10-B fragment (FIG. 6). In contrast the 20-C haplotype shows a 16 Kg carcass weight improvement in this analysis over the 20-B haplotype.

Figure 7:
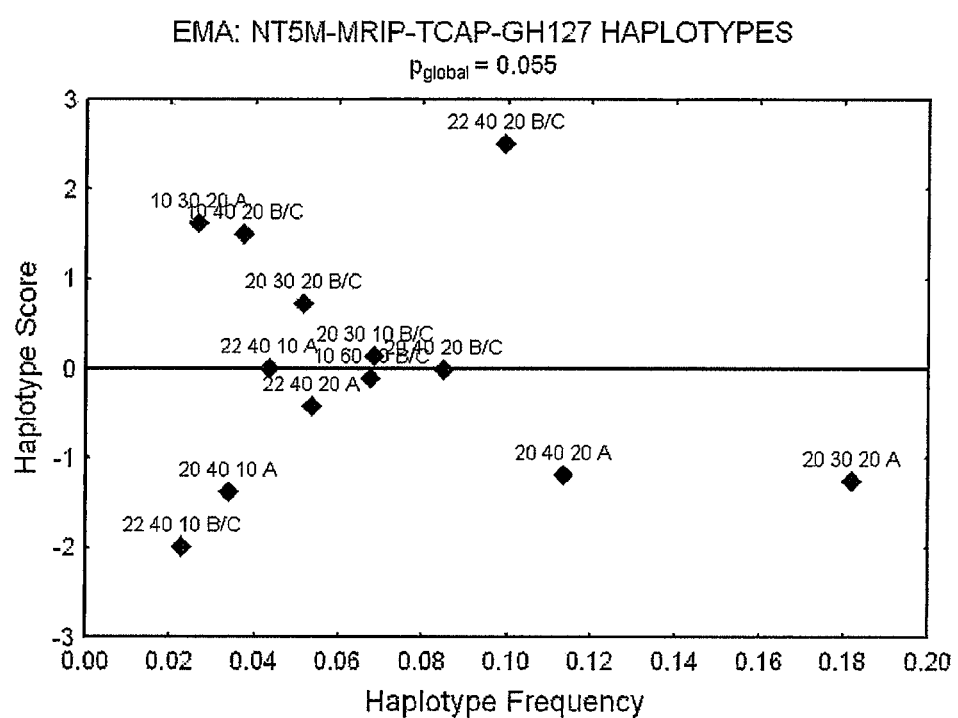
FIG. 7 shows the correlation between SREBP1 to GH haplotype frequencies and eye muscle area.

Of particular interest are the significant correlation signals for Eye Muscle Area (EMA) a key indicator of tenderness and meat quality. This is associated with certain alleles at loci extending from NT5M to GH (FIG. 7). In particular, a positive association with EMA was noted with haplotype (NT5M-MRIP-TCAP-GH) 22-40-20 B/C and to a lesser extent with of 10-30-20 A, 10-40-20-B/C. Negative associations with EMA in this analysis noted particularly with haplotypes 20-30-20-A and 20-40-20-A, and to a lesser extend with 22-40-10-B/C.

Figure 8:
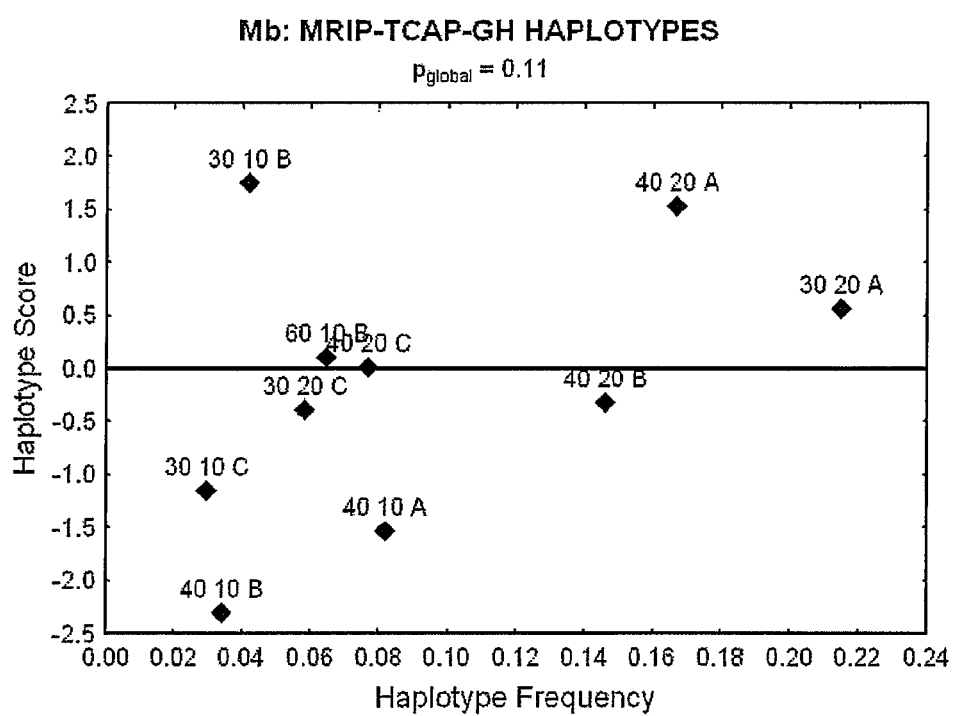
FIG. 8 shows the correlation between MRIP to GH haplotypes and marbling.

For MRIP-TCAP-GH haplotypes and Marbling Score, there are multiple contributions across the haplotype for marbling—positively for 30-10-B and 40-20-A haplotypic fragments and negatively for 40-10-B, 40-10-A and 30-10-C (FIG. 8).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2009904511 filed 17 Sep. 2009, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Hoashi et al. (2007) Mammalian Genome 18:880-886.
Jiang et al. (2008) International Journal of Biological Sciences 4:345-351.
Rincker et al. (2006) Journal of Animal Science 84:686-693.
Van Eenennaam et al. (2007) Journal of Animal Science 85:891-900.

The invention claimed is:

1. A method of genotyping a livestock animal with a desired trait, comprising:
analyzing a genotype of the livestock animal by using probes or primers to identify a polymorphism in a M-RIP gene, wherein the polymorphism comprises a difference in a length in a region bounded by a M-RIP primer pair, wherein a primer of the M-RIP primer pair comprises:

```
                                    (SEQ ID NO: 1)
5'-AGG GGT GCT GAG TCT ACA GG-3'.
```

2. The method of claim 1, wherein the desired trait is at least one of a marbling, a level of monounsaturated fats in muscle tissue, a types monounsaturated fats in muscle tissue, a ratio of monosaturated fat in muscle tissue, a carcass weight, a meat quality, a speed of finishing, a feedlot efficiency or a consumer preference.

3. The method of claim 1, wherein the primer comprises a detection label.

4. The method of claim 1, wherein the length of the polymorphism is about 192 bp or about 193 bp.

5. The method of claim 1, wherein the length of the polymorphism is between about 201 bp and about 203 bp.

6. The method of claim 1, wherein the length of the polymorphism is about 208 bp or about 209 bp.

7. The method of claim 1, wherein the length of the polymorphism is between about 218 bp and about 220 bp.

8. The method of claim 1, further comprising identifying a SREBP associated polymorphism in an SREBP-1 gene, wherein the SREBP associated polymorphism comprises a difference in a length in a region bounded by a SREBP-1 primer pair, wherein the SREBP-1 primer pair comprises:

```
                                    (SEQ ID NO: 7)
5'-CCA CAA CGC CAT CGA GAA ACG CTA C-3', and (SEQ ID NO: 8)
5'-GGC CTT CCC TGA CCA CCC AAC TTA G-3'.
```

9. The method of claim 8, wherein the length of the SREBP associated polymorphism is between about 428 bp and about 432 bp.

10. The method of claim 8, wherein the length of the SREBP associated polymorphism is between about 343 bp and about 346 bp.

11. The method of claim 1, further comprising identifying a NT5M associated polymorphism in an NT5M gene, wherein the NT5M associated polymorphism comprises a difference in a length in a region bounded by an NT5M primer pair, wherein the NT5M primer pair comprises:

```
                                    (SEQ ID NO: 3)
5'-GGA AGG CCA GTT ACA TGG CA-3', and (SEQ ID NO: 4)
5'-CAC AAC CAA GGC CAA AAT CGC A-3'.
```

12. The method of claim 11, wherein the length of the NT5M associated polymorphism is about 321 bp.

13. The method of claim 11, wherein the length of the NT5M associated polymorphism is about 331 bp.

14. The method of claim 11, wherein the length of the NT5M associated polymorphism is about 334 bp.

15. The method of claim 1, further comprising identifying a polymorphism in a TCAP gene, wherein the TCAP associated polymorphism comprises a differences in a length of a region bounded by a TCAP primer pair, wherein the TCAP primer pair comprises:

```
                                    (SEQ ID NO: 5)
5'-AGT ACC AGC TGC CCT ACC A-3', and (SEQ ID NO: 6)
5'-CTG AGA CAT GGA GCG AGC CA-3'.
```

16. The method of claim 15, wherein the length of the TCAP associated polymorphism is between about 230 bp and about 235 bp.

17. The method of claim 15, wherein the length of the TCAP associated polymorphism is about 245 bp.

18. A method of genotyping a livestock animal with a desired trait, comprising:
analyzing a genotype of the livestock animal using probes or primers to identify a polymorphism associated with a M-RIP gene on chromosome 19 to identify one allele of four potential alleles, wherein the four potential alleles correspond to a length of the polymorphism in a region of the M-RIP gene amplified with a M-RIP primer pair, wherein a M-RIP primer of the M-RIP primer pair comprises:

```
                                    (SEQ ID NO: 1)
5'-AGG GGT GCT GAG TCT ACA GG-3',
``` wherein the length of the polymorphism in the region of the M-RIP gene amplified with the M-RIP primer pair is:
about 192 bp or about 193 bp corresponding to a first allele;
between about 201 bp and about 203 bp corresponding to a second allele;
about 208 bp or about 209 bp corresponding to a third allele; or
between about 218 bp and about 220 bp corresponding to a fourth allele.

19. The method of claim 18, wherein the M-RIP primer of the M-RIP primer pair further comprises:

```
                                    (SEQ ID NO: 2)
5'-CTC CAG GAG GCA GGA GAA G-3'.
```

20. The method of claim 18, further comprising:
identifying a SREBP-1 associated polymorphism in an SREBP-1 gene, wherein the SREBP-1 associated polymorphism comprises a difference in a length of the SREBP-1 gene in a region bounded by a SREBP-1 primer pair, wherein the SREBP-1 primer pair comprises:

```
                                    (SEQ ID NO: 7)
5'-CCA CAA CGC CAT CGA GAA ACG CTA C-3'; and (SEQ ID NO: 8)
5'-GGC CTT CCC TGA CCA CCC AAC TTA G-3';
``` wherein the SREBP-1 associated polymorphism is one of:
the length of the SREBP-1 associated polymorphism is between about 428 bp and about 432 bp; or
the length of the SREBP-1 associated polymorphism is between about 343 bp and about 346 bp;

identifying a NT5M associated polymorphism in an NT5M gene, wherein the NT5M associated polymorphism comprises a difference in a length of a region bounded by a NT5M primer pair, wherein the NT5M primer pair comprises:

```
                                           (SEQ ID NO: 3)
5'-GGA AGG CCA GTT ACA TGG CA-3'; and (SEQ ID NO: 4)
5'-CAC AAC CAA GGC CAA AAT CGC A-3';
``` wherein the NT5M associated polymorphism is one of:
the length of the NT5M associated polymorphism is about 321 bp;
the length of the NT5M associated polymorphism gene is about 331 bp; or
the length of the NT5M associated polymorphism gene is about 334 bp;
identifying a TCAP associated polymorphism in a TCAP gene, wherein the TCAP associated polymorphism comprises a difference in a length of a region bounded by a TCAP primer pair, wherein the TCAP primer pair comprises:

```
                                           (SEQ ID NO: 5)
5'-AGT ACC AGC TGC CCT ACC A-3'; and (SEQ ID NO: 6)
5'-CTG AGA CAT GGA GCG AGC CA-3';
``` wherein TCAP associated polymorphism is one of:
the length of the TCAP associated polymorphism is between about 230 bp and about 235 bp; or
wherein the length of the TCAP associated polymorphism is about 245 bp.

21. The method of claim 1, wherein the M-RIP primer pair further comprises:

```
                                           (SEQ ID NO: 2)
5'-CTC CAG GAG GCA GGA GAA G-3'.
```

\* \* \* \* \*